United States Patent [19]

Fischell et al.

[11] Patent Number: 5,607,442
[45] Date of Patent: Mar. 4, 1997

[54] STENT WITH IMPROVED RADIOPACITY AND APPEARANCE CHARACTERISTICS

[75] Inventors: Robert E. Fischell, Dayton, Md.; David R. Fischell, Fair Haven, N.J.

[73] Assignee: IsoStent, Inc., San Carlos, Calif.

[21] Appl. No.: 557,355

[22] Filed: Nov. 13, 1995

[51] Int. Cl.$^6$ .................................................. A61M 29/00
[52] U.S. Cl. ........................ 606/191; 606/198; 606/195; 623/1; 623/12
[58] Field of Search .................................. 606/198, 191; 623/1, 12

[56] References Cited

U.S. PATENT DOCUMENTS

| | | | |
|---|---|---|---|
| 4,768,507 | 9/1988 | Fischell et al. | 128/303 |
| 5,176,617 | 1/1993 | Fischell et al. | 600/3 |
| 5,201,314 | 4/1993 | Bosley et al. | 128/654 |
| 5,211,658 | 5/1993 | Clouse | 606/191 |

*Primary Examiner*—Michael Powell Buiz
*Assistant Examiner*—Kevin Truong

[57] ABSTRACT

A stent (10) is plated with a high density, radiopaque metal (or alloy) such as gold or tantalum. Specifically, the stent (10) is plated to a sufficient thickness (15) on its longitudinal wires (12) to make it clearly radiopaque in fluoroscopy, but the generally circumferential wires (11) are plated to a much lesser thickness (14) so that they are not distinctly radiopaque. Before the stent (10) is deployed radially outward in a vessel of the human body, the longitudinal wires (12) are very close together so the implanting physician can easily discern the proximal and distal extremities of the stent (10). Furthermore, the physician can readily discern that the stent (10) has been deployed because the longitudinals (12) will separate to an increased distance from each other after proper deployment. Still further, if the stent does not properly deploy, fluoroscopy will indicate that there is an indentation (12A) or (12C) in one or more longitudinal hence informing the physician that he should inflate a high pressure balloon at the end of a balloon angioplasty catheter to further deploy the stent (10) radially outward against the inner wall of the vessel. Proper stent deployment is characterized by a generally parallel relationship between opposite longitudinal wires (12). Because the stent (10) has a single metal outer coating (albeit of varying thickness) on all stent outer surfaces, electrolytic corrosion of the stent (10) is avoided. Furthermore, there may be other advantages associated with plating a stent (10) with a greater thickness on some wires and a lesser thickness on others. Still further, a stent (10) that is gold plated over all its surfaces would provide a most attractive appearance.

17 Claims, 4 Drawing Sheets

STENT WITH IMPROVED RADIOPACITY AND APPEARANCE CHARACTERISTICS

BACKGROUND

Stents made from stainless steel or Nitinol are very difficult to visualize under fluoroscopy. Stents made from tantalum are typically so radiopaque that they obscure some of the lumen within an implanted stent. Some stents are made with a radiopaque coating (viz., gold) on only their most proximal and most distal portions thus providing knowledge of the stents position in a vessel without obscuring most of the volume within the stent. However, such stents do not provide any knowledge as to whether the stent is fully deployed throughout its entire length so as to make contact against the inner surface of the vessel wall. Furthermore, a stent that is gold plated only on its end portions is not as attractive in appearance as a stent that is uniformly gold plated. Furthermore, a stent that is gold plated on one (or more) section(s) and not gold plated on another section can cause an electrolytic corrosion that can compromise the structural integrity of the stent.

SUMMARY OF THE INVENTION

The present invention is a stent that is plated with a high density, radiopaque metal (or alloy) such as gold or tantalum. Specifically, the stent is plated to a sufficient thickness on its longitudinal wires to make it clearly radiopaque in fluoroscopy, but the generally circumferential wires are plated to a much lesser thickness so that they are not distinctly radiopaque. Before the stent is deployed radially outward in a vessel of the human body, the longitudinal wires are very close together so the implanting physician can easily discern the proximal and distal extremities of the stent. Furthermore, the physician can readily discern that the stent has been deployed because the longitudinals will separate to an increased distance from each other after proper deployment. Still further, if the stent does not properly deploy, fluoroscopy will indicate that there is an indentation in one or more longitudinals hence informing the physician that he should use a high pressure balloon at the end of a balloon angioplasty catheter to further deploy the stent against the inner wall of the vessel. Proper stent deployment is characterized by a generally parallel relationship between opposite longitudinal wires. When this generally parallel condition is observed, the physician need not utilize an intravascular ultrasound (IVUS) catheter to ascertain correct stent deployment. By obviating the need for using an IVUS catheter, the stent of the present invention provides a considerable saving in the time and cost for discerning proper implantation of a stent.

Because the stent has a single metal outer coating (albeit of varying thickness) on all stent outer surfaces, electrolytic corrosion of the stent is avoided. Furthermore, a stent that is gold plated over all its surfaces would provide a most attractive appearance.

Thus, it is an object of the present invention to place a radiopaque metal coating of sufficient thickness on the longitudinal wires of a stent so that these and only these wires are clearly discernible in fluoroscopy.

Another object of this invention is that all wires other than longitudinal wires be plated with the same metal as the longitudinal wires except that those wires have a sufficiently thin metal coating so that they are not clearly discernible under fluoroscopy.

Still another object of this invention is that making only the longitudinal wires radiopaque allows the implanting physician to know that the stent is properly deployed without requiring the utilization of an IVUS catheter.

Still another object of this invention is that having the radiopaque metal over the stent entire exterior surface disallows electrolytic corrosion of the metal of the stent.

Still another object of this invention is that a stent that is plated over its entire surface (particularly if gold plated) would provide an attractive appearance.

These and other important objects and advantages of this invention will become apparent from the detailed description of the invention and the associated drawings provided herein.

DETAILED DESCRIPTION OF THE INVENTION

Figure 1:
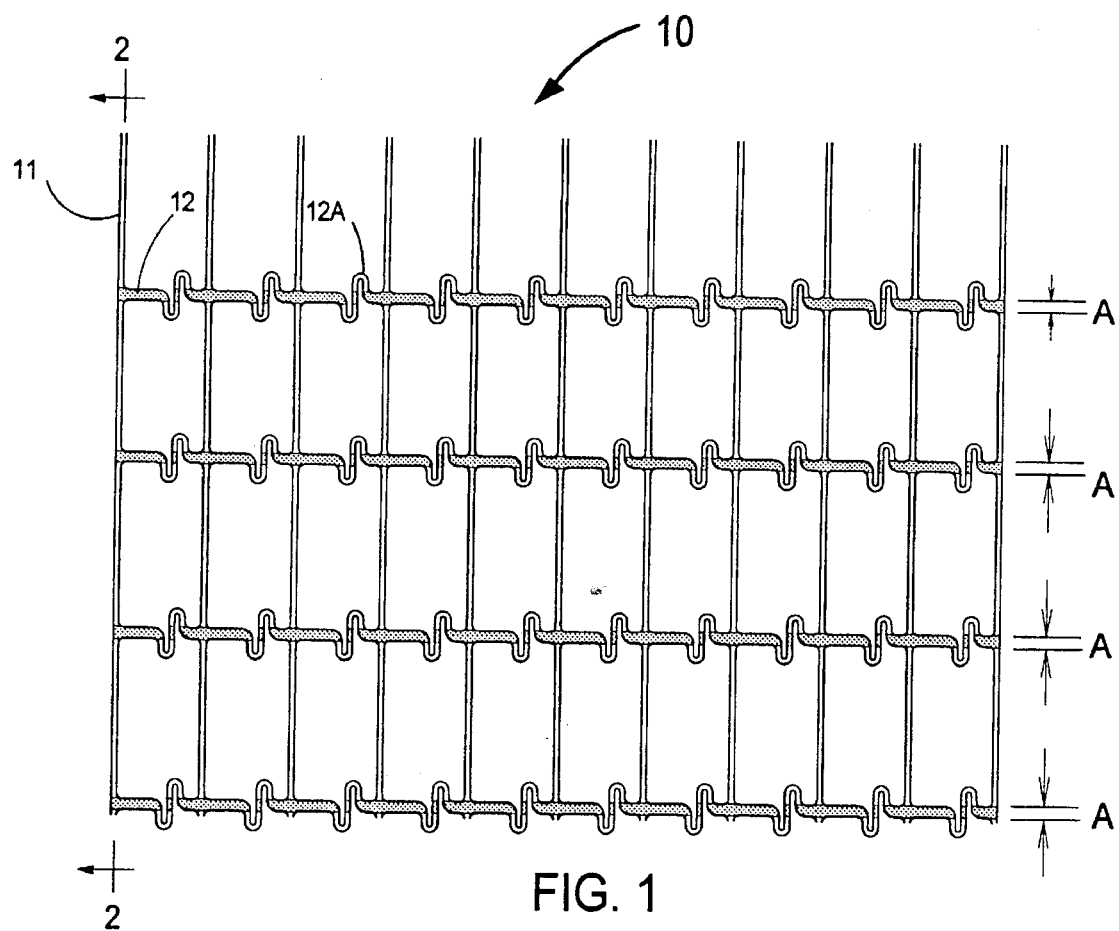
FIG. 1 illustrates a cylindrical stent as it would appear opened up into a flat, two-dimensional form.

FIG. 1 illustrates a stent 10 laid out into a flat, two-dimensional form. In fact, the stent 10 is in the form of a thin-walled, cylindrical mesh having a plurality of rings 11, two or more longitudinals 12 having undulating structures 12A to enhance the longitudinal flexibility of the stent 10. The design advantages of this type of stent structure is described in U.S. patent application Ser. No. 08/202,128 entitled "Stent Having A Multiplicity of Closed Circular Structures" which application is included herein by reference.

The entire stent 10 is plated with a dense metal such as gold, platinum or tantalum. Of these, gold is preferable because of its high density and excellent appearance. The gold plating would be much thicker in the region "A" which covers the longitudinals 12 and extends slightly onto the rings 11 as is more clearly shown in FIGS. 2 and 3.

Figure 2:
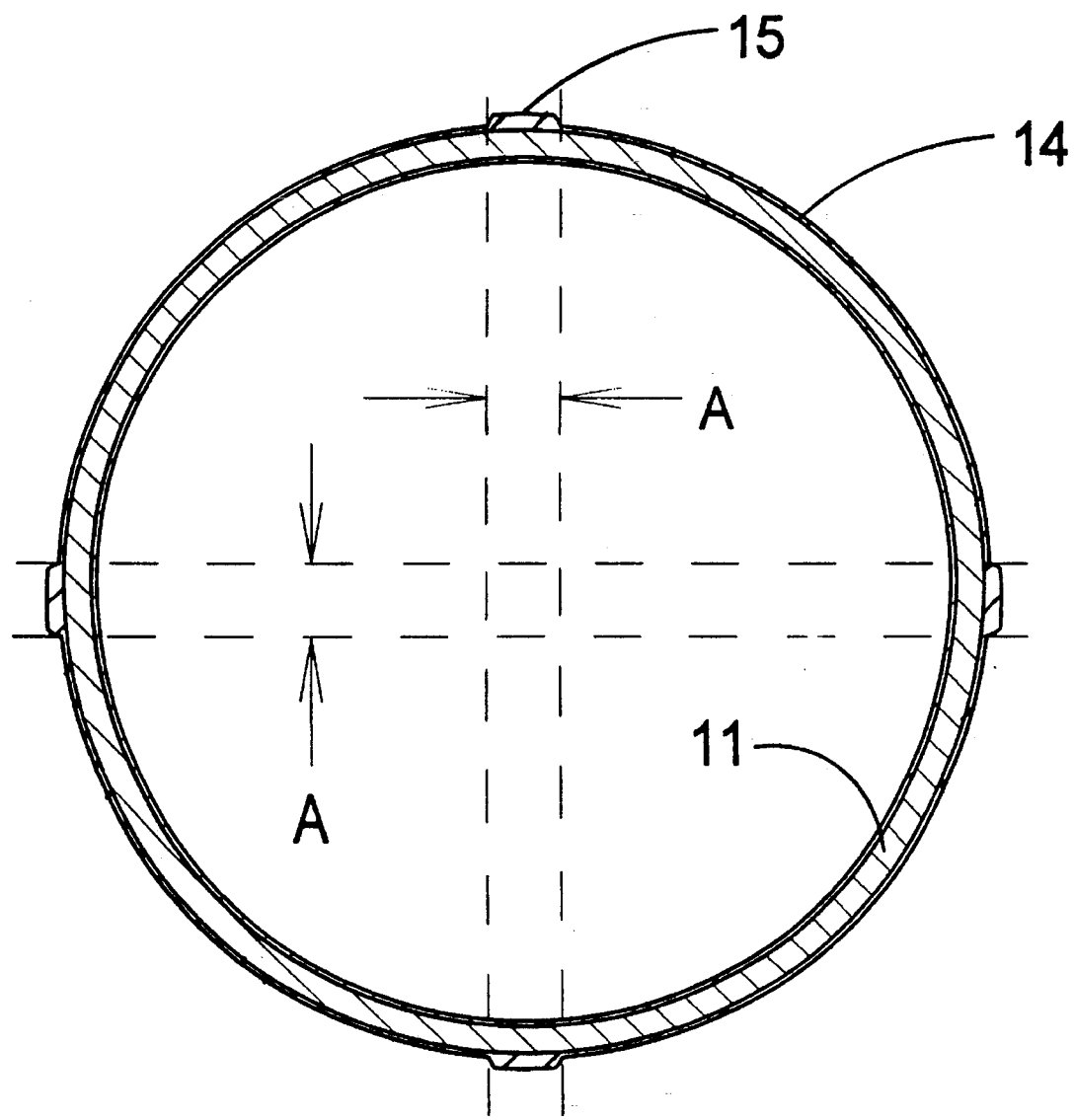
FIG. 2 is a cross section of one ring of the stent in its actual, cylindrical form at section 2—2 of FIG. 1.
Figure 3:
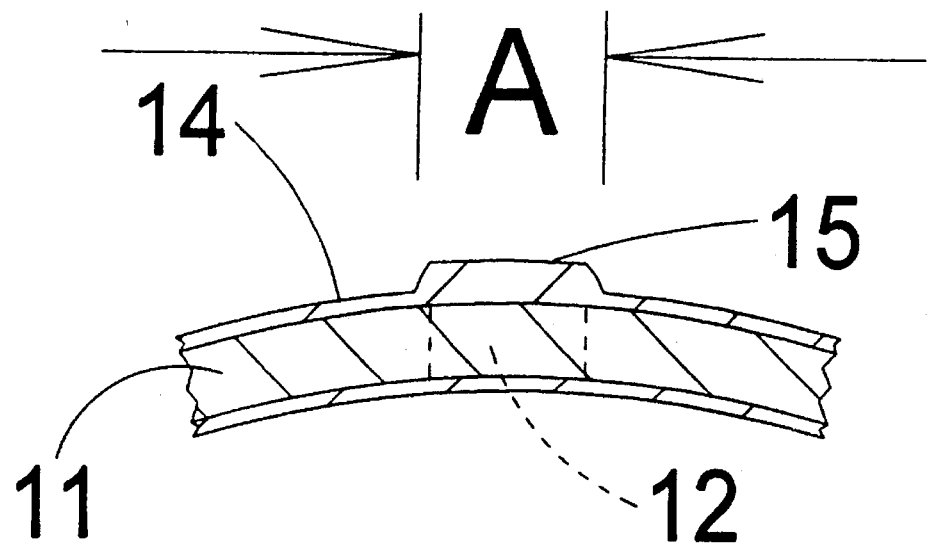
FIG. 3 is a highly enlarged cross section of the stent at the place where a longitudinal wire intersects a circumferential (or ring) wire.

FIGS. 2 and 3 show a cross section of the ring 11 of the stent 10. FIGS. 2 and 3 show a thick gold plating 15 in the region "A" (mostly on the longitudinals) and a much thinner coating 14 on the ring 11. Although the thicker coating 15 is shown on one side of a longitudinal, the coating could also be thicker on the opposite side of the longitudinal. It is also desireable to have the thick coating 15 only within the region "A" and not extended onto most of the surface of the rings 11. However, since the stent 10 would probably be formed from stainless steel or a shape memory alloy such as Nitinol, it would be desirable to have the entire external surface of the stent covered with one dense metal (such as gold) to preclude any electrolytic corrosion of the metal of the stent when it is placed in the blood stream and to enhance the stent's appearance.

Figure 4A:
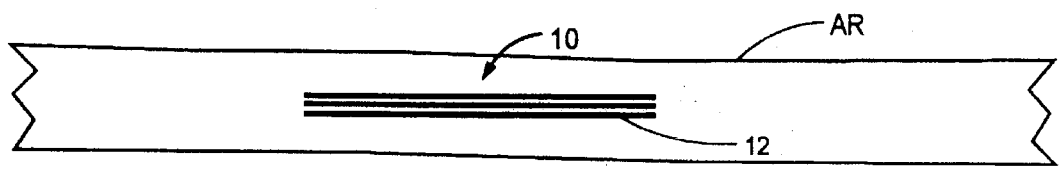
FIG. 4A illustrates how the stent would look in fluoroscopy prior to deployment in an artery.
Figure 4B:
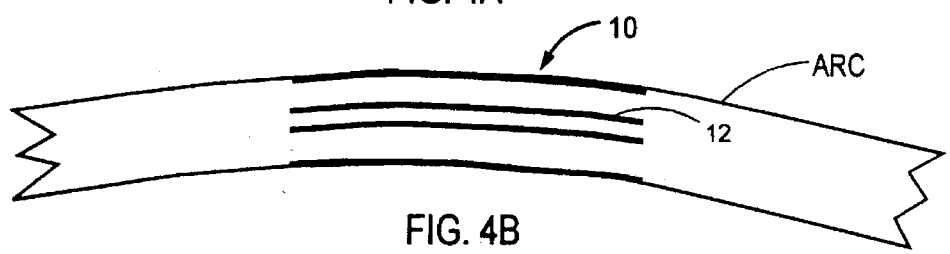
FIG. 4B illustrates how the stent would look in fluoroscopy after proper deployment in a curved artery.
Figure 4C:
FIG. 4C illustrates how the stent would look in fluoroscopy after proper deployment in a straight artery.

FIGS. 4A to 4C inclusive illustrate how the stent 10 of the present invention would appear under fluoroscopy. FIG. 4A shows the stent 10 having longitudinals 12 prior to deployment. Because the longitudinals 12 are very close together, they become even more discernible in fluoroscopy. This is important so that the interventional cardiologist can accurately place the stent 10 within an artery AR.

FIG. 4B illustrates proper deployment of the stent 10 in a curved artery ARC. From FIG. 4B we see that fluoroscopy would show that the longitudinals 12 are parallel and deployed outward. By taking perpendicular views with the fluoroscopy equipment, the cardiologist can determine that each pair of opposite longitudinals 12 are placed near the outer edge of the artery ARC (or AR) and that each longitudinal 12 of a pair of oppositely located longitudinals 12 is parallel to the other longitudinal in that pair.

FIG. 4C shows the same proper deployment of the stent 10 in a straight artery AR as described for the curved artery ARC.

Figure 4D:
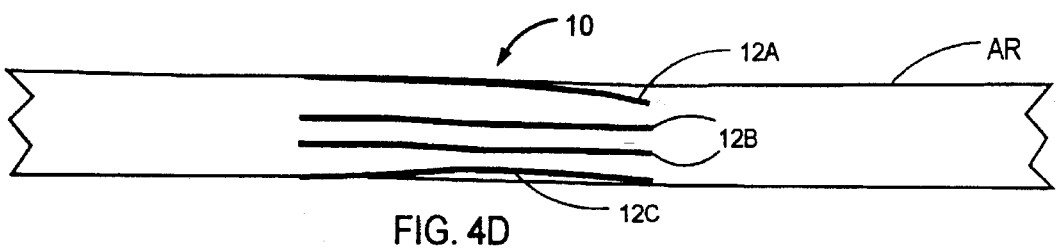
FIG. 4D illustrates how the stent would look in fluoroscopy after improper deployment in a straight artery.

FIG. 4D, on the other hand, shows that an opposite pair of longitudinals 12A and 12C are each improperly deployed. Longitudinal 12A is not fully deployed near one of its ends, and longitudinal 12 is not fully deployed near its center. The opposite pair of longitudinals 12B appear in this view to be properly deployed, however, a final determination of proper deployment of the longitudinals 12B can be obtained only by moving the fluoroscopy by 90° to obtain an orthogonal view of the stent 10. When the cardiologist observes non-straight deployment of one or more longitudinals 12, he or she would attempt to properly deploy the stent 10 by inflating within the stent a very high pressure balloon located near the distal end of a balloon angioplasty catheter. This technique is well known in the art and science of interventional cardiology (or radiology). By use of this technique, the cardiologist can be assured that the stent 10 is properly placed without requiring an intravascular ultrasound (IVUS) catheter to verify proper stent deployment. Eliminating the need for an IVUS catheter saves considerable time and money.

Figure 5:
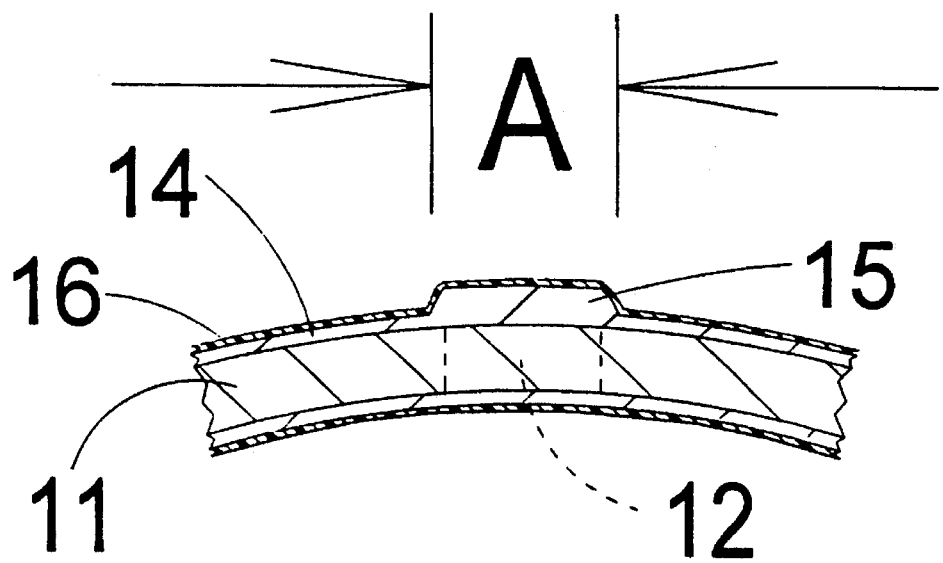
FIG. 5 illustrates a highly enlarged cross section of the stent of the present invention which includes an anti-thrombogenic coating.

FIG. 5 shows a highly enlarged cross section of the ring 11 with a thin gold plating 14 and a longitudinal 12 with a thick gold plating 15. The thickness of the high density metal plating would typically be greater than 5 microns on the longitudinals 12 and less than one-half that thickness on the rings 11. More optimally the longitudinal plating thickness would be greater that 10 microns and the rings less than 1 micron. One could have the dense metal on either one side or both sides of the longitudinals 12. The dense metal plating can be accomplished by electroplating, vapor deposition or any similar process. Masking can be used to apply thicker plating to the longitudinals as compared to the rings.

FIG. 5 also illustrates an anti-thrombogenic coating 16 which can be used to prevent blood clots from forming on the stent 10. The coating 16 could be covalently bonded heparin, a special plastic covering or any similar material.

It is also conceived that the stent includes a radioisotope that is incorporated by ion implantation into the metal of the stent or is placed on the stent below the anti-thrombogenic coating. Such a radioisotope (viz., phosphorous 32) can be employed to decrease neointimal hyperplasia subsequent to stent implantation.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A stent for deployment within a vessel of a human body comprising:

a generally tubular, thin-walled, metal structure having a longitudinal axis, the stent including a multiplicity of longitudinal structures each lying generally parallel to the longitudinal axis of the stent and having a surface plating of a high density metal, the high density metal being at least 5 microns in thickness on at least some portion of the surface of each longitudinal structure; and, the stent also having generally circumferential metal wires connected to the longitudinal structures, said wires being plated with said dense metal to a lesser thickness as compared to a greater thickness of dense metal thickness on the longitudinal structures.

2. The stent of claim 1 wherein most of the metal of the stent is a stainless steel.

3. The stent of claim 1 wherein most of the metal of the stent is a shape memory alloy.

4. The stent of claim 3 wherein the shape memory alloy is Nitinol.

5. The stent of claim 1 wherein the ratio of the thickness of the plating on the longitudinal structures is at least twice the thickness of the plating on the generally circumferential wires that are connected to the longitudinal structures.

6. The stent of claim 1 wherein all structures and wires of the stent are plated on all surfaces with the high density metal.

7. The stent of claim 1 wherein the high density metal plating on the longitudinal structures is gold.

8. The stent of claim 1 wherein the stent includes two longitudinal structures.

9. The stent of claim 1 wherein the stent includes four longitudinal structures.

10. The stent of claim 1 wherein a radioisotope material is placed within the metal of the stent.

11. The stent of claim 1 wherein at least some portion of the stent includes a radioisotope material.

12. A method for determining if a stent is properly deployed within a vessel of a human body, the method comprising the following steps:

(a) fabricate a thin-walled cylindrical stent having a longitudinal axis, the stent being radiopaque along at least one pair of generally longitudinal structures that are each parallel to the longitudinal axis of the cylindrical stent;

(b) deploy the at least one pair of radiopaque structures of the stent outward against the vessel wall; and, (c) observe by fluoroscopy if each longitudinal structure of the at least one pair of radiopaque longitudinal structures remains generally parallel to the other line of that pair of radiopaque lines.

13. A stent for deployment within a vessel of a human body comprising a generally tubular, thin-walled metal structure consisting of at least two different sets of wire-like structures, the at least two sets including a first set of wire-like structures and a second set of wire-like structures, all sets of wire-like structures being plated with a high density metal with the first set of wire-like structures having a thickness of plating that is at least twice the thickness of the plating of the second set of wire-like structures.

14. The stent of claim 13 wherein most of the metal of the stent is a stainless steel.

15. The stent of claim 13 wherein most of the metal of the stent is a shape memory alloy.

16. The stent of claim 15 wherein the shape memory alloy is Nitinol.

17. The stent of claim 13 wherein the high density metal plating on the wire-like structures is gold.

* * * * *